(12) United States Patent
Graeber et al.

(10) Patent No.: US 8,809,305 B2
(45) Date of Patent: *Aug. 19, 2014

(54) ADMINISTRATION OF ADAPALENE AND BENZOYL PEROXIDE FOR THE LONG-TERM TREATMENT OF ACNE VULGARIS

(75) Inventors: Michael Graeber, Lawrenceville, NJ (US); Yin Liu, Princeton Junction, NJ (US); Barbara Gore, Cranbury, NJ (US)

(73) Assignee: Galderma Research & Development, Biot (FR)

( * ) Notice: Subject to any disclaimer, the term of this patent is extended or adjusted under 35 U.S.C. 154(b) by 1034 days.

This patent is subject to a terminal disclaimer.

(21) Appl. No.: 12/458,982

(22) Filed: Jul. 29, 2009

(65) Prior Publication Data

US 2010/0029762 A1 Feb. 4, 2010

Related U.S. Application Data

(63) Continuation of application No. PCT/EP2008/051155, filed on Jan. 30, 2008.

(60) Provisional application No. 60/898,113, filed on Jan. 30, 2007.

(51) Int. Cl.
*A61K 31/60* (2006.01)
*A61P 17/10* (2006.01)
*A61K 31/235* (2006.01)
*A61K 31/70* (2006.01)

(52) U.S. Cl.
USPC ............. 514/165; 514/544; 514/24; 514/859; 514/714

(58) Field of Classification Search
USPC ........................................................ 514/544
See application file for complete search history.

(56) References Cited

U.S. PATENT DOCUMENTS

| | | | |
|---|---|---|---|
| 5,733,886 A * | 3/1998 | Baroody et al. | 514/24 |
| 6,559,189 B2 * | 5/2003 | Baker et al. | 514/642 |
| 7,642,288 B2 | 1/2010 | Graeber et al. | |
| 2003/0170196 A1 | 9/2003 | Orsoni et al. | |
| 2008/0181963 A1 | 7/2008 | Orsoni et al. | |

FOREIGN PATENT DOCUMENTS

| | | |
|---|---|---|
| WO | WO 03/055472 A | 7/2003 |
| WO | WO 2006/079563 A1 | 8/2006 |
| WO | WO 2008/006888 A | 1/2008 |

OTHER PUBLICATIONS

Wen-Wen et al., "Clinical efficacy and safety of 5% benzoyl peroxide gel combined with 0.1% adapalene gel in the treatment of acne vulgaris: a multicenter randomized study", Database Biosis, Biosciences Information Service, Jun. 2003, Database accession No. PREV200300514701, pp. 310-312, vol. 36, No. 6.*
Gollnick et al. (P01.75 Evaluation of a maintenance treatment of acne vulgaris with adapalene gel, 0.1%. JEADV (2004) 18 (Suppl. 2), 193-557).*
Caron et al., "Skin tolerence of adapalene 0.1% gel in combination with other topical antiacne treatments," *Journal of the American Academy of Dermatology*, vol. 36, No. 6, pp. S113-S115, Jun. 1, 1997, XP005177985.
Capizzi et al., "Skin tolerability and efficacy of combination therapy with hydrogen peroxide stabilized cream and adapalene gel in comparison with benzoyl peroxide cream and adapalene gel in common acne. A randomized, investigator-masked, controlled trial," *British Journal of Dermatology*, vol. 151, No. 2, pp. 481-484, Jan. 1, 2004, XP008073258.
Korkut et al., "Benzoyl Peroxide, Adapalene, and Their Combination in the Treatment of Acne Vularis," *Journal of Dermatology*, vol. 32, No. 3, pp. 169-173, Jan. 1, 2005, XP009075640.
Do Nascimento et al., "Single-blind and comparative clinical study of the efficacy and safety of benzoyl peroxide 4% gel (BID) and adapalene 0.1% gel (QD) in the treatment of acne vulgaris for 11 weeks," *Journal of Dermatological Treatment*, vol. 14, No. 3, pp. 166-171, Jan. 1, 2003, XP008073256.
Leyden, James et al., "Comparison of Treatment of Acne Vulgaris With Alternate-Day Applications of Tazarotene 0.1% Gel and Once-Daily Applications of Adapalene 0.1% Gel: A Randomized Trial," *Cutis*, Jun. 2001, pp. 10-16, vol. 67.
Differin-Adapalene Data Sheet, product insert as of Nov. 1998, pp. 1-5.
International Search Report for Corresponding PCT/EP2008/051155 dated Jun. 26, 2008.

* cited by examiner

*Primary Examiner* — Layla Soroush
(74) *Attorney, Agent, or Firm* — Dentons US LLP (57) ABSTRACT

A regimen for the safe and effective long-term treatment of acne vulgaris entails topically applying onto the affected skin area of a subject afflicted therewith, for a period of time of at least four (4) months, e.g., for at least twelve (12) months and advantageously on a daily basis and preferably once a day, a thus effective amount of a topical medicament containing adapalene and benzoyl peroxide, formulated into a pharmaceutically acceptable medium therefor.

11 Claims, 3 Drawing Sheets

ADMINISTRATION OF ADAPALENE AND BENZOYL PEROXIDE FOR THE LONG-TERM TREATMENT OF ACNE VULGARIS

CROSS-REFERENCE TO EARLIER APPLICATIONS

This application is a continuation of PCT/EP2008/051155, filed Jan. 30, 2008 and designating the United States (published in the English language on Aug. 7, 2008 as WO 2008/092911 A1), which claims benefit of U.S. Provisional Application No. 60/898,113, filed Jan. 30, 2007, each hereby expressly incorporated by reference in its entirety and each assigned to the assignee hereof.

BACKGROUND OF THE INVENTION

1. Technical Field of the Invention

The present invention relates to the administration of a composition (topical medicament) comprising adapalene and benzoyl peroxide (BPO) to a patient in need so as to provide a long-term treatment of acne vulgaris.

2. Description of Background and/or Related and/or Prior Art

Acne vulgaris is a common skin disorder that makes up 20% of the visits to a dermatology practice, and affects the majority of the teenage population. Management of acne is challenging, especially when considering the chronicity of the disease and the variability in response to treatment.

The management of acne often requires combination therapy and a long-term therapeutic strategy (for example, Thiboutot D. New treatments and therapeutic strategies for acne. *Arch Family Med* 2000; 9: 179-187; Gollnick H, Cunliffe W, Berson D, et al., Management of acne, a report from a Global Alliance to Improve Outcomes in Acne. *J Am Acad Dermatol.* 2003; 49(1 suppl): S1-S37). Maintenance therapy is necessary for many acne patients, as acne lesions have been shown to recur after discontinuing a successful treatment regimen. (Gollnick H, Cunliffe W, Berson D, et al., Management of acne, a report from a Global Alliance to Improve Outcomes in Acne. *J Am Acad Dermatol.* 2003; 49(1 suppl): S1-S37; Thielitz A, Helmdach M, Ropke E-M, Gollnick H. Lipid analysis of follicular casts from cyanoacrylate strips as a new method for studying therapeutic effects of antiacne agents. *Br J Dermatol.* 2001; 145: 19-27). Long-term therapy is necessary for many acne patients to achieve the desired reduction of acne lesions as well as to increase the likelihood of maintaining short-term improvements of this commonly recurring condition (Tenaud I et al., In vitro modulation of TLR-2, CD1d and IL-10 by adapalene on normal human skin and acne inflammatory lesions *Exp. Dermatol.* 2007 June; 16(6): 500-6; and Thiboutot D M et al., Treatment considerations for inflammatory acne: clinical evidence for adapalene 0.1% in combination therapies, *J Drugs Dermatol.* 2006 September; 5(8): 785-94. Review. Erratum in: *J Drugs Dermatol.* 2007 January; 6(1):table of contents).

Despite the variety of medications available for the treatment of acute acne, there are few studies with respect to the safety and efficacy of the long-term treatment of patients with acne vulgaris.

Currently, the most effective comedolytic agents are oral isotretinoin and topical retinoids. (Cunliffe W J, Holland D B, Clark S M, Stables, G I. Comedogenesis: some new aetiological, clinical and therapeutic strategies. *Br J Dermatol.* 2000; 142: 1084-1091). Oral isotretinoin is an impractical choice for long-term therapy due to the potential for toxicity and teratogenicity. Topical anti-acne medication such as retinoids, could be associated with elevated skin irritation, so careful consideration must be given to the tolerability of a potential maintenance therapy. Cutaneous side effects may decrease the likelihood of treatment adherence, particularly when treating an asymptomatic condition. (Koo J. How do you foster medication adherence for better acne vulgaris management *SKINmed.* 2003; 2: 229-33; and Haider A, Shaw J C. Treatment of acne vulgaris. *JAMA.* 2004; 292: 726-735).

Available topical and systemic therapies for the treatment of acne include retinoids, benzoyl peroxide (BPO), antibiotics, and hormonal therapy. Since acne vulgaris involves multiple etiological factors including follicular hyperkeratinization, increased sebum production, P. acnes proliferation, and inflammation, (Thiboutot D M et al., Treatment considerations for inflammatory acne: clinical evidence for adapalene 0.1% in combination therapies, *J Drugs Dermatol.* 2006 September; 5(8): 785-94. Review. Erratum in: *J Drugs Dermatol.* 2007 January; 6(1): table of contents; Pariser D M, Westmoreland P, Morris A, Gold M H, Liu Y, Graeber M. Long-term safety and efficacy of a new fixed-dose combination of adapalene 0.1% to benzoyl peroxide 2.5% for the treatment of acne vulgaris. *J Drugs Dermatol.* 2007; 6(9): 899-905; Thiboutot D M, Bucko A, Eichenfield L, et al., Adapalene-benzoyl peroxide, a new fixed-dose combination for the treatment of acne vulgaris: results of a randomized, multi-centre, double-blind, controlled study. *J Am Acad Dermatol. doi:* 10.1016/j.jaad 2007.06.006. Published online Jul. 24, 2007) combination therapy utilizing agents with complementary mechanisms, such as a topical retinoid and an antimicrobial, is used as part of a long-term therapeutic strategy.

Current guidelines recommend early initiation of combination therapy with topical retinoids and antimicrobials for all but the most severe cases of acne, followed by topical retinoid maintenance therapy with or without benzoyl peroxide (BPO) (Thiboutot DM et al., *J Drugs Dermatol.* 2006 September; 5(8): 785-94. Review. Erratum in: *J Drugs Dermatol.* 2007 January; 6(1): table of contents). Although the administration of additional agents increases the complexity of a treatment regimen, combination therapy is effective at addressing the multifaceted pathophysiological nature of acne. Fixed-dose combination products may help reduce the complexity of acne management for patients and physicians by reducing the number of medications a patient has to remember to take on a daily basis, thereby potentially increasing treatment adherence. Despite the possible benefits, there are relatively few fixed-dose combination products available for the treatment of acne. Several BPO-antibiotic combinations are available in addition to one product that combines a topical retinoid with a topical antibiotic (Harkaway K S, McGinley K J, Foglia A N et al., Antibiotic resistance patterns in coagulase-negative staphylococci after treatment with topical erythromycin, benzoyl peroxide, and combination therapy. *Br J Dermatol.* 1992; 126(6): 586-90; Thielitz A, Krautheim A, Gollnick H. Update in retinoid therapy of acne. *Dermatol Ther.* 2006; 19(5): 272-9; Adapalene-benzoyl peroxide, a new once daily fixed-dose combination for the treatment of acne vulgaris: a randomized, bilateral (split-face), dose-assessment study of cutaneous tolerability in healthy subjects. Cutis. Submitted).

However, there are currently no combination products with BPO and a topical retinoid, a combination that would be consistent with both the short-term and long-term treatment recommendations from the acne guidelines.

Therefore, need exists for an efficient and safe drug complying with both short term and long-term acne treatment.

SUMMARY OF THE INVENTION

The present invention features a safe and efficient composition comprising adapalene and benzoyl peroxide used for the long-term treatment of acne vulgaris.

Therefore, a first embodiment of the present invention is the administration of a composition, which is in a preferred embodiment a fixed dose combination, comprising adapalene and BPO formulated as a topical medicament, to a patient in need so as to provide a long-term treatment of acne vulgaris, wherein the administration pattern of the topical medicament comprises administering a therapeutically effective amount of the composition for at least 4 months, preferably for at least 6 months, more preferred for at least 9 months, preferentially for at least 12 months.

The topical medicament is administered on a daily basis and preferably once a day. In another embodiment the topical medicament is administered every two days and preferably once a day. In both cases, the topical medicament is administered in the evening after wash.

DETAILED DESCRIPTION OF BEST MODE AND SPECIFIC/PREFERRED EMBODIMENTS OF THE INVENTION

In a preferred embodiment, the topical medicament is a gel composition.

The topical medicament comprises at least 0.001% of adapalene by weight and preferentially comprises 0.01% to 2% by weight of adapalene relative to the total weight of the composition, preferably comprises 0.01 to 0.5% by weight, most preferred 0.1 to 0.3%. The medicament comprises also 0.025% to 20% by weight of BPO, preferably comprises 0.5% to 10% by weight of BPO, most preferred 2% to 10%, preferentially 2.5 to 5% by weight of BPO relative to the total weight of the composition.

Another embodiment of the invention is the formulation of a composition comprising adapalene and BPO into a topical medicament for administering to a patient so as to sustain its biological response in the treatment of acne vulgaris, wherein the administration pattern of the topical medicament comprises applying to afflicted skin from 0.01% to 0.5% by weight of adapalene and from 2% to 10% by weight of BPO relative to the total weight of the composition for at least 4 months, preferably at least 6 months; more preferred for at least 9 months; preferably for at least 12 months.

Particularly, one embodiment of the present invention is the administration of a composition comprising adapalene and BPO (topical medicament) to a patient so as to sustain its biological response in the treatment of acne vulgaris, wherein the administration pattern of the topical medicament comprises applying to afflicted skin 0.1% by weight of adapalene and 2.5% by weight of BPO once daily for at least 6 months, preferentially for at least 9 months, more preferred for at least 12 months.

According to these embodiments, the topical medicament is applied to afflicted skin which contains preferentially from 20 to 100 non-inflammatory lesions, and/or from 20 to 50 inflammatory lesions, and no active nodules or cysts and in preferred embodiment the composition is a gel composition.

In another embodiment, the present invention features a regimen of providing long-term treatment of acne vulgaris in a patient in need thereof, comprising topically applying on afflicted skin an effective amount of a composition comprising adapalene and peroxide benzoyle in an acceptable pharmaceutical medium. The composition is topically applied for at least 4 months, prefentially applied for at least 6 months, preferably for at least 9 months, more preferred for at least 12 months.

The term "pharmaceutically acceptable medium" means a medium that is compatible with the skin, mucous membranes and the integuments.

The term "fixed combination" should be understood as meaning a combination whose active principles are combined at fixed doses in the same vehicle/medium (single formula) that delivers them together to the point of application. Preferably, the pharmaceutical composition in the form of a fixed combination is a gel; in this case, the two active principles are dispersed and intimately mixed, during the manufacture, in the same vehicle, which delivers them together during the application of the gel.

More specifically, the present invention provides the assessment of the long-term clinical profile of this fixed-dose combination, in 12-month study evaluating the safety and efficacy of the once-daily adapalene-BPO fixed-dose combination gel in the treatment of subjects with acne vulgaris when used once daily for up to 12 months.

The present invention also provides efficient compositions for dermatological afflictions allowing once-daily application and pleasant use for the patient.

However, formulation of a composition comprising BPO and retinoids presents difficulties.

First of all, BPO efficiency is related to its decomposition when contacted with skin. Indeed, with decomposition the oxidative properties of free radicals provide the desirable effect. Regarding the optimal efficiency of BPO, it is thus crucial to prevent its decomposition while in storage.

In addition, BPO is an unstable compound that renders its formulation difficult in formulated products.

BPO solubility and stability were studied by Chellquist et al., in ethanol, in propylene glycol and in mixtures of polyethylene glycol 400 (PEG 400) and water (Chellquist E. M. et Gorman W. G., *Pharm. Res.*, 1992, Vol. 9: 1341-1346). The authors commented that BPO in solution is degrading more or less according to the solvent and its concentration.

BPO degradation time in PEG 400 (0.5 mg/g), in ethanol and in propylene glycol are respectively 14, 29 and 53 days at 40° C. Such a degradation in not compatible with commercialized products.

Another technical problem to be solved for the formulation of a composition comprising both adapalene and BPO is the chemical and physical compatibility of these compounds within the same formulation provided that common retinoids are natural oxidization sensitive, visible light and ultra violet sensitive and BPO being a strong oxidizing agent.

Indeed, BPO triggers rapidly degradation of natural oxidization sensitive retinoids: 50% of tretinoine is degraded within 2 hours and 95% is degraded within 24 hours.

Contrary thereto, in view of the composition of the invention where adapalene is the retinoid, no adapalene degradation had appeared within 24 hours.

In the context of the present invention, BPO can be used in the free or encapsulated form, for instance adsorbed BPO form or absorbed BPO form within any porous support. It might be for instance encapsulated BPO within polymeric system constituted by porous microspheres like microsponges marketed under the trademark—Microsponges P009A Benzoyle peroxyde by Cardinal Health company.

Adapalene (6-[3-(1-adamantyl)-4-methoxyphenyl]-2-naphthoic acid) is a naphthoic acid derivative with potent retinoid and anti-inflammatory properties. Adapalene was developed for the topical treatment of acne vulgaris and other retinoid-sensitive dermatoses including various disorders of keratinization, proliferation and differentiation. Adapalene acts mainly by regulating differentiation of keratinocytes (comedolytic effect and preventing new comedones), but also has anti-inflammatory activity. In particular, adapalene is a well-tolerated topical retinoid.

Adapalene is marketed under the brand name Differin® at a weight concentration of 0.1%, in the form of an "alcoholic lotion" solution, an aqueous gel and a cream. These compositions are useful for treating acne.

The present invention encompasses also the salts of adapalene. By salts of adapalene are meant the salts formed with a pharmaceutically acceptable base, especially mineral bases such as sodium hydroxide, potassium hydroxide and ammonia or organic bases such as lysine, arginine or N-methylglucamine. The term "adapalene salts" also means the salts formed with fatty amines such as dioctylamine and stearylamine.

WO 03/055472 moreover describes stable pharmaceutical compositions comprising adapalene and benzoyl peroxide (BPO).

Reported non-serious adverse reactions associated with adapalene include common signs and symptoms of local irritative reactions (erythema, peeling, dry skin, pruritus, burning and stinging), rare cases of local allergic reactions (edema at the application site, contact eczema or dermatitis), or other skin and appendage disorders (very rare cases of hypopigmentation and hyperpigmentation, photosensitivity reactions, hair thinning, hair growth, skin erosion following facial waxing).

However, adapalene and other effective retinoids were studied only in short-term (12 weeks) clinical trials. Therefore, there is a need to develop a safe and effective method of long-term treatment of acne vulgaris moreover without inducing bacterial resistance.

BPO is a well established antimicrobial agent, is more effective than topical antibiotics on P acnes suppression, with no evidence of microorganism resistance.[2,]. Because retinoids do not create selective pressure for resistance, this combination is expected to decrease the incidence of epidermal bacterial resistance relative to an antibiotic.

In addition, as shown in example below, the composition of the present invention which is a fixed-dose combination of adapalene and benzoyle peroxide (BPO) was well tolerated in the current long-term study, with a similar safety and tolerability profile as adapalene monotherapy.

Advantageously, the present compositions comprise from 0.0001 and 20% by weight of BPO and from 0.0001 and 20% by weight of adapalene relative to the total weight of the composition; preferentially respectively from 0.025 and 10% by weight of BPO and from 0.01% to 2% by weight of adapalene relative to the total weight of the composition.

Preferably and as an example, in compositions for treating acne, BPO is used with concentrations from 2% to 10% by weight and preferentially from 2.5% to 5% by weight relative to the total weight of the composition. Adapalene is used in this kind of composition in concentration from 0.01% to 1% by weight and preferentially from 0.01% to 0.5%, most preferred 0.1% to 0.3% by weight relative to the total weight of the composition.

Advantageously, adapalene and BPO particles are sized such that at least 80% of particles and preferably at least 90% of particles have a diameter of less than 25 µm and at least 99% of particles have a diameter of less than 100 µm.

One aspect of the present invention is to provide an effective method of treating acne vulgaris on a long-term basis by using a composition combining adapalene and BPO.

Another aspect of the present invention is to provide a long-term treatment of acne vulgaris with superior efficacy and comparable tolerability by using higher strengths of adapalene and BPO as compared to short-term studies.

The present invention also features a method for treating a patient afflicted with acne vulgaris comprising topically applying to afflicted skin region of the patient a topical medicament (which is here a dermatological preparation) comprising a therapeutically effective amount of a composition comprising adapalene and BPO at least every two days, preferably at least once every two days. More preferably, the composition is administered on a daily basis, preferably once daily for at least 6 months, more preferably once daily for at least 12 months.

The topical medicament, which is a dermatological preparation, can be applied to the afflicted skin region in the evening after wash, preferably once daily.

More specifically, the present invention provides the formulation of adapalene and BPO into a topical medicament for administering to a patient so as to sustain its biological response in the treatment of acne vulgaris, wherein the administration pattern of the topical medicament comprises administering 0.1% by weight of adapalene and 2.5% by weight of BPO once daily for more than 3 months, preferably for at least 4 months, more preferably for at least 6 months, more preferred for at least 9 months, most preferred for at least 12 months.

This invention also features a method of long-term treatment of acne vulgaris comprising topically applying to afflicted skin of a patient a topical medicament comprising 0.1% by weight of adapalene and 2.5% by weight of BPO once daily for more than 3 months, preferably for at least 4 months, more preferably for at least 6 months, more preferred for at least 9 months, most preferred for at least 12 months.

The topical medicament is in a form compatible with topical administration and particularly is a form of gel, cream, lotion, emulsion, suspension.

Preferably, the topical medicament is a gel composition and more preferred is an aqueous gel composition comprising 0.1% by weight of adapalene and 2.5% by weight of BPO and is applied to the afflicted skin for at least 4 months, more preferably for at least 6 months, most preferred for at least 9 months, preferably for at least 12 months. The topical medicament is particularly efficient when the afflicted skin contains 20 to 100 non-inflammatory lesions, 20 to 50 inflammatory lesions, and no active nodules or cysts.

For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

Median Percent Change in Lesion Counts (ITT Population, Observed Data, and Month 12 LOCF)

Endpoint: the last available data observed during the study. Baseline value was used if no post-Baseline data were available.

"Final" means the last available data observed during the post-baseline period.

"Worst" means the data observed with the highest severity during the post-baseline period.

The present invention provides a regimen for the long-term treatment of acne vulgaris by the use of a gel composition containing 0.1% by weight of adapalene and 2.5% by weight of Benzoyle Peroxide. Such product is described in WO 03/055472. The following details a study that clearly demonstrates the clinical benefit of long-term treatment of acne with the above mentioned composition.

To further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE

Clinical Test of Long-term Treatment of Acne Vulgaris with a Fixed-Dose Combination Gel Containing Adapalene 0.1% to BPO 2.5% by Weight/Total Composition Weight Study Design and Subjects:

The long-term safety and efficacy of a fixed combination gel of adapalene-BPO were evaluated in a multicenter, open-label, single-arm study conducted at 28 centers in the United States. Subjects with acne vulgaris applied once-daily adapalene-BPO to the face for up to 12 months. Safety and efficacy evaluations were performed at baseline, week 1, week 2, and at months 1, 2, 4, 6, 8, 10, and 12. A urine pregnancy test was required at baseline and at the final study visit for all females of childbearing potential. Subjects were free to withdraw from the study at any time and for any reason. Subjects not completing the entire study were to be fully evaluated when possible.

A total of 452 subjects enrolled in 28 study centers in the United States. All 452 subjects applied study medication at least once, and were analyzed in both the Safety and Efficacy (ITT) populations. Male and female subjects, 12 years of age or older, with 30 to 100 non-inflammatory facial lesions, 20 to 50 inflammatory facial lesions, and no active nodules or cysts were enrolled in the study. Specified washout periods were required for subjects taking certain topical and systemic treatments. Exclusion criteria prohibited enrollment of subjects with severe acne requiring isotretinoin therapy or other dermatologic conditions requiring interfering treatment. Women were excluded if they were pregnant, nursing, or planning a pregnancy as were men with facial hair that would interfere with the assessments.

TABLE 1

Summary of Subject Demographics and Baseline Characteristics (ITT Population):

| Variable | Total (N = 452) |
| --- | --- |
| Gender | |
| Male | 222 (49.1%) |
| Female | 230 (50.9%) |
| Total | 452 (100.0%) |
| Age (Years) | |
| N | 452 |
| Mean | 18.3 |
| S.D. | 6.62 |
| Median | 16.0 |
| Min, Max | 12, 50 |
| Age Category (Years) | |
| 12 to 17 | 299 (66.2%) |
| 18 to 64 | 153 (33.8%) |
| 65 and Above | 0 |
| Total | 452 (100.0%) |
| Race | |
| Caucasian | 345 (76.3%) |
| Black | 53 (11.7%) |
| Asian | 10 (2.2%) |
| Hispanic | 31 (6.9%) |
| Other | 13 (2.9%) |
| Total | 452 (100.0%) |
| Skin Photo Type | |
| I | 12 (2.7%) |
| II | 105 (23.2%) |
| III | 162 (35.8%) |
| IV | 87 (19.2%) |
| V | 61 (13.5%) |
| VI | 25 (5.5%) |
| Total | 452 (100.0%) |

Safety and Efficacy Assessments:

Safety and tolerability were assessed through evaluations of local facial tolerability and adverse events. At each visit, the investigator rated erythema, scaling, dryness, stinging/burning on a scale ranging from 0 (none) to 3 (severe). Adverse events were evaluated at each visit. Routine laboratory data (hematology, blood chemistry, and urinalysis) were collected at screening, month 6, and month 12.

The efficacy variables were percent lesion count reduction from baseline (total, inflammatory, and non-inflammatory) and subject's assessment of acne (on a scale from 0 [complete improvement] to 5 [worse]). Lesion counts were assessed on the face only, excluding the nose.

Efficacy and Safety Variables:

Table 2 is a flow chart of assessed measurements during this study.

TABLE 2

Flow Chart of Efficacy and Safety Measurements:

| Parameter | Screening | Baseline | Wk 1 & 2 | Months 1, 2 & 4 | Month 6 | Month 8 | Month 10 | Month 12/ Early Termination Visit |
|---|---|---|---|---|---|---|---|---|
| Efficacy | | | | | | | | |
| Lesion Counts | X | X | X | X | X | X | X | X |
| Subject's Assessment of Acne | | | | | X | | | X |
| Safety | | | | | | | | |
| Local Tolerability | | X | X | X | X | X | X | X |
| Adverse Events | | X | X | X | X | X | X | X |
| Blood & Urine Sampling | X | | | | X | | | X |

Wk = Week
M = Month

The Investigator (or responsible designee) conducted efficacy evaluations consisting of non-inflammatory lesion counts (open and closed comedones) and inflammatory lesion counts (papules and pustules) and nodules/cysts. Lesion counts were taken from the face only. Subject's assessment of acne was also documented.

Non-inflammatory and inflammatory lesions were counted on the forehead, left and right cheeks, and chin above the jaw line (excluding the nose). Total lesion counts were calculated by the Sponsor. The following definitions were used:

Non-inflammatory Lesions:
Open Comedone: A mass of sebaceous material that is impacted behind an open follicular orifice (blackhead).
Closed Comedone: A mass of sebaceous material that is impacted behind a closed follicular orifice (whitehead).

Inflammatory Lesions
Papule: A small, solid elevation less than one centimeter in diameter.
Pustule: A small, circumscribed elevation of the skin that contains yellow-white exudate.
Nodule/Cyst: A circumscribed, elevated lesion generally more than 1.0 cm in diameter.

Subjects evaluated their facial acne at the Month 6 and Month 12/Early Termination Visit, as compared to the Baseline Visit, according to the following scale:

TABLE 3

| | |
|---|---|
| 1 | Marked Improvement |
| 2 | Moderate Improvement |
| 3 | Minimal Improvement |
| 4 | No Change |
| 5 | Worse |

The safety variables evaluated were: local tolerability (erythema, scaling, dryness, and stinging/burning), Adverse Events (AEs), and routine laboratory data (hematology, blood chemistry, and urinalysis). Side effects expected during treatment with topical retinoids include erythema, scaling, dryness, and stinging/burning. During the study, the course of these expected events was assessed as local tolerability.

Erythema, scaling, dryness, and stinging/burning were rated on the following scales:

TABLE 4

Erythema: abnormal redness of the skin:

| None | 0 | No erythema |
|---|---|---|
| Mild | 1 | Slight pinkness present |
| Moderate | 2 | Definite redness, easily recognized |
| Severe | 3 | Intense redness |

TABLE 5

Scaling: abnormal shedding of the stratum corneum:

| None | 0 | No scaling |
|---|---|---|
| Mild | 1 | Barely perceptible shedding, noticeable only on light scratching or rubbing |
| Moderate | 2 | Obvious but not profuse shedding |
| Severe | 3 | Heavy scale production |

TABLE 6

Dryness: brittle and/or tight sensation:

| None | 0 | No dryness |
|---|---|---|
| Mild | 1 | Slight but definite roughness |
| Moderate | 2 | Moderate roughness |
| Severe | 3 | Marked roughness |

TABLE 7

| | | Stinging/Burning: prickling pain sensation immediately after (within 5 minutes of) dosing: |
|---|---|---|
| None | 0 | No stinging/burning |
| Mild | 1 | Slight warm, tingling/stinging sensation; not really bothersome |
| Moderate | 2 | Definite warm, tingling/stinging sensation that is somewhat bothersome |
| Severe | 3 | Hot, tingling/stinging sensation that has caused definite discomfort |

Erythema, scaling, and dryness were evaluated by the Investigator. Stinging/burning was recorded by the Investigator after discussion with the subject.

Local tolerability measures of the signs and symptoms of skin irritation were considered adverse effects only if the severity of the expected signs and symptoms was such that an interruption of the subject's participation in the study, at his/her request or at the Investigator's discretion, had occurred. Altered dosing regimens (such as every other day dosing) to manage irritation were not considered to be an interruption of the subject's participation in the study.

Adverse Events (AEs):

An AE was defined as any unfavorable and unintended sign, symptom, or disease temporally associated with the use of a medicinal (investigational) product, whether or not related to the investigational product. Any new sign, symptom or disease, or clinically significant increase in the intensity of an existing sign, symptom or disease, was considered an AE. This included any new signs or symptoms suffered by the subject after accidental or intentional overdose or misuse. Lack of efficacy of the study drug was not considered an AE unless it led to other unfavorable medical occurrences. However, clinically significant worsening of the treated disease was considered an AE.

Pregnancy was not considered an AE but was an important medical event.

Severity of an AE was rated as mild, moderate, or severe. Relationship of an AE to study drug was rated as: related (possibly, probably or definitely related) or unrelated (unlikely or definitely unrelated).

Serious Adverse Events (SAEs):

An SAE was defined as any untoward medical occurrence that at any dose:
Resulted in death
Was life-threatening (i.e., the subject was at risk of death at the time of the event, but not an event which hypothetically might have caused death if it were more severe)
Required inpatient hospitalization or prolongation of an existing hospitalization (hospitalization solely for diagnostic tests, even if related to an adverse event, elective hospitalization for any intervention planned before subject entered the study, or admission to a day-care facility did not themselves constitute an SAE)
Resulted in persistent or significant disability/incapacity or
Resulted in a congenital anomaly/birth defect, or
other important medical events that jeopardized the subject or required intervention to prevent one of the outcomes listed above.
Routine Laboratory Tests:
Blood and urine samples were obtained according to the schedule specified in the study flow chart of Table 1. The following blood chemistries were evaluated: protein, albumin, globulin, A/G ratio, bilirubin (total), alanine transaminase (ALT), aspartate transaminase (AST), alkaline phosphate, gamma-glutamyl transferase GGT, lactic dehydrogenase (LDH), blood urea nitrogen (BUN), creatinine, uric acid, cholesterol (total), triglycerides, and glucose.

The following hematology parameters were evaluated: hematocrit, hemoglobin, red cell count, mean corpuscular volume (MCV), mean corpuscular hemoglobin (MCH), mean corpuscular hemoglobin concentration (MCHC), white cell count, and platelet count.

A routine urinalysis for the following was performed: color, appearance, specific gravity, urine reaction pH, glucose, protein (qualitative.), ketones, occult blood, bilirubin, nitrite, and leukocytes.

Statistical Analyses:

As this was an open-label study, only descriptive data presentations were made. No formal statistical hypotheses were tested. Descriptive statistics were used to summarize all data. For continuous variables, the number of subjects (N), mean, standard deviation (SD), median, minimum and maximum are provided for the data collected at each visit and the changes/percent changes from baseline at each post-baseline visit. For categorical variables, frequencies and percentages for each category are provided.

All summaries for subject characteristics and efficacy data were based on the Intent to Treat (ITT) population (this population consisted of all subjects enrolled, to whom study medication was dispensed). All safety data is based on the safety population (all subjects who applied study drug at least once).

Analysis visits were imputed according to an algorithm to summarize data by the treatment duration. If multiple measurements were present within the same interval, the measurement closest to the target study day was used for analysis. If two measurements were taken with equal differences in timing compared with the target day, data from the nominal visit number (recorded on the case report form) was used for analysis. For example, if measurements were collected on Day 360 and Day 367, the data collected at Day 360 was used for analysis at Month 12 while data collected at Day 367 was used in analysis for endpoint. Although all data were used in imputing the visits for analysis, some data were not used for analysis due to multiple observations within a visit window.

Subject data for all treated subjects were summarized by four quarters of the study: "Baseline to <3 months", "3 months to <6 months", "6 months to <9 months", and "9 months to 1 year." The number of subjects at risk for each period (i.e., subjects available at beginning of each period) was tabulated. The number of subjects at risk is determined based on each subject's treatment duration. Each month was considered to be 30 days for these calculations, and a 7-day visit window was used. Thus, "Baseline to <3 months" is Day 1 through Day 82, "3 months to <6 months" is Day 83 through Day 172, "6 months to <9 months" is Day 173 through Day 262, "9 months to <1 year" is Day 263 through Day 352, and "1 year and above" is Day 353 and above.

By the same principle, subject completion/discontinuation was summarized by subjects and by four quarters. The discontinuation rate for each quarter was calculated by the number of subjects who discontinued within the period divided by the number of subjects at risk for the given period.

The planned safety variables to be analyzed were as follows:

1. Local Tolerability Assessment (Erythema, Scaling, Dryness, Stinging/Burning) was to be evaluated at Baseline and each post-Baseline visit on a "0" (=None) to "3" (=Severe) scale.
2. AEs were to be assessed at each visit.
3. Routine laboratory data (haematology, blood chemistry, urinalysis) were to be collected at Screening, Month 6 and Month 12/Early Termination Visit.

The planned efficacy variables to be analyzed were:

1. Percent change from Baseline in facial Inflammatory, Non-inflammatory, and Total Lesion Counts at scheduled post-Baseline visits.
2. Subject's Assessment of Acne on a "5" (Worse) to "0" (Complete Improvement) scale at Month 6 and Month 12/Early Termination Visit.

The Non-inflammatory Lesion Count was the sum of open comedones and closed comedones. The Inflammatory Lesion Count was the sum of papules and pustules. The other Lesion Count was the sum of nodules and cysts. The Total Lesion Count was the sum of Inflammatory, Non-inflammatory, and other Lesions. Subject's Assessment of Acne was evaluated on a 5 (Worse) to 0 (Complete Improvement) scale.

The intent-to-treat (ITT) population was defined as all subjects enrolled, to whom medication was dispensed. The safety population was defined as all subjects enrolled who had applied study medication at least once. Subjects with major protocol deviations were to be tabulated. No per-protocol (PP) population was defined for this study.

All data analyses were carried out according to a pre-established analysis plan. The sample size of 450 was selected to ensure approximately 300 subjects would be exposed to adapalene-BPO for at least 6 months and 100 subjects would be exposed for up to 1 year. All safety data were summarized based on the safety population. Adverse events were tabulated in frequency tables and summarized by quarters to evaluate the adverse event profile over time. Tolerability variables (erythema, scaling, dryness, stinging/burning) were summarized by severity score. A shift table for the laboratory data at screening versus last post-baseline visit was tabulated for each laboratory parameter. All efficacy data were summarized based on the ITT population. Lesion count data collected at each visit and the changes and percent changes from baseline at post-baseline visits were summarized. Subject's assessment of acne was tabulated. Descriptive statistics were used to summarize the data. No formal statistical hypotheses were tested.

The safety population was defined as all patients randomized and treated at least once. The intent-to-treat (ITT) population included all randomized subjects who were dispensed study medication. At each time point, efficacy assessments were evaluated using observed data as well as using last observation carried forward methodology (LOCF). Subjects with major protocol deviations were to be tabulated. No per-protocol (PP) population was defined for this study.

Results:

Subject Disposition and Baseline Characteristics:

A total of 452 subjects were enrolled in the study (table 1). All 452 subjects applied study medication at least once and were analyzed in the ITT and safety populations. A total of 397 (87.8%) subjects were evaluated for 3 months or more, 366 (81.0%) were evaluated for 6 months or more, and 334 (73.9%) were evaluated for 9 months or more. Overall, 327 (72.3%) of subjects completed the 12-month study. The mean (±SD) extent of exposure was 294.6 days (±117.7). No subjects discontinued due to lack of efficacy and discontinuations due to adverse events were low (2.0%). The baseline characteristics of the ITT population are summarized in Table I.

Figure 1:
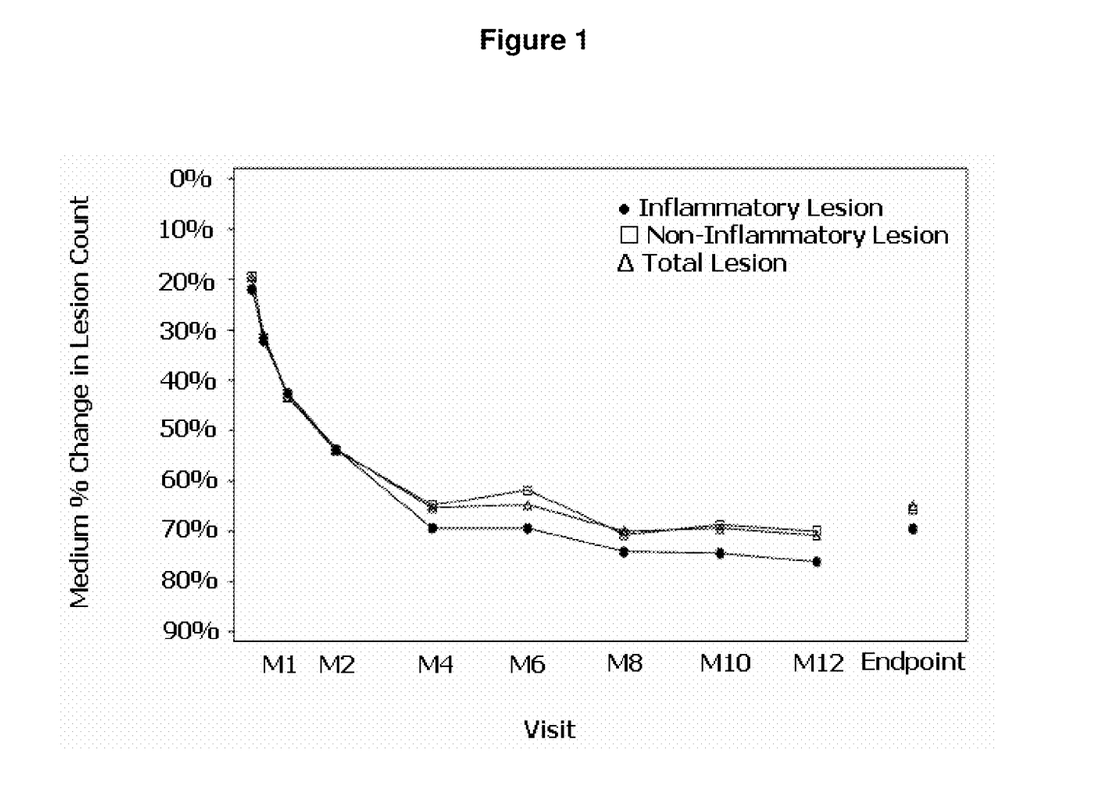
FIG. 1 shows a time course of median percentage change in lesion counts.

Efficacy Evaluation:

The results for percent change in lesion counts in the ITT Population are shown in FIG. 1 and table 8.

TABLE 8

Summary of Inflammatory, Non-inflammatory, and Total Lesion Counts: Median Counts at Baseline and Median Percent Change from Baseline at Each Visit and at Month 12 LOCF (ITT Population):

| Time-point | N | Inflammatory Lesion Count | N | Non-inflammatory Lesion Count | N | Total Lesion Count |
|---|---|---|---|---|---|---|
| Baseline Count | 452 | 27.0 | 452 | 42.0 | 452 | 72.0 |
| Week 1 | 423 | −21.9% | 423 | −19.3% | 423 | −19.4% |
| Week 2 | 429 | −32.1% | 429 | −31.7% | 429 | −31.0% |
| Month 1 | 415 | −42.5% | 415 | −43.3% | 415 | −43.2% |
| Month 2 | 426 | −53.7% | 426 | −54.0% | 426 | −53.7% |
| Month 4 | 390 | −69.3% | 390 | −64.8% | 390 | −65.4% |
| Month 6 | 361 | −69.4% | 361 | −61.9% | 361 | −64.8% |
| Month 8 | 341 | −74.1% | 341 | −70.6% | 341 | −70.1% |
| Month 10 | 329 | −74.4% | 329 | −68.8% | 329 | −69.4% |
| Month 12 | 327 | −76.0% | 327 | −70.0% | 327 | −70.8% |
| Month 12 LOCF | 452 | −69.5% | 452 | −65.7% | 452 | −64.9% |

For the 327 subjects who remained in the study until Month 12 visit (observed data), the percent reductions in total, inflammatory and non-inflammatory lesion counts were 70.8%, 76% to 70% respectively. When ITT LOCF data are considered, the median percent reductions from baseline in total, inflammatory, and non-inflammatory lesion counts were 64.9%, 69.5%, and 65.7% at Month 12, respectively. Reductions in inflammatory, non-inflammatory, and total lesions were observed starting as early as Week 1. For patients remaining in the study, lesion counts continued to decrease through the initial 4 months of the study and the reductions were maintained for the duration of the study.

The subject assessment demonstrated a clinical improvement with 12 months of adapalene-BPO treatment. At the end of the study, 330 subjects (330/411, 80.3%) reported a moderate, marked, or complete improvement, 45 subjects (45/411, 10.9%) reported a minimal improvement, and 36 subjects (36/411, 8.8%) reported no change or worsening. The results were similar regardless of age, gender, or race.

FIG. 1 illustrates the effect of adapalene-BPO combination therapy on facial acne during the course of the 12-month study.

TABLE 9

Summary of Subject's Assessment of Acne (ITT Population, Month 12 Observed Data, and Month 12 LOCF):

| Subjects Assessment of Acne | Month 6 | Month 12 | Month 12 LOCF |
|---|---|---|---|
| 0 = Complete Improvement | 17 (4.7%) | 40 (12.2%) | 43 (10.5%) |
| 1 = Marked Improvement | 149 (41.5%) | 164 (50.2%) | 193 (47.0%) |
| 2 = Moderate Improvement | 147 (40.9%) | 77 (23.5%) | 94 (22.9%) |
| 3 = Minimal Improvement | 31 (8.6%) | 37 (11.3%) | 45 (10.9%) |
| 4 = No Change | 11 (3.1%) | 6 (1.8%) | 20 (4.9%) |
| 5 = Worse | 4 (1.1%) | 3 (0.9%) | 16 (3.9%) |
| Total | 359 (100.0%) | 327 (100.0%) | 411 (100.0%) |

Month 12 LOCF: the last available data observed during the study carried forward. Baseline value was used if no post-Baseline data were available.

Safety Evaluation:

Local Tolerability Assessment:

Local tolerability variables (erythema, scaling, dryness, and stinging/burning) were summarized by a severity score on a 4-point scale at each visit (0=none to 3=severe). Each subject's "Worst" score and the "Final" score were summarized where "Worst" was the highest score and "Final" was the last observation during the post-baseline period.

The number of subjects whose local tolerability data were worse (higher score) than their Baseline score was tabulated at each post-baseline visit. The "Worst" and "Final" scores for each subject, if higher than Baseline were tabulated.

recorded in the first post-baseline study visit (week 1) and then decreased to levels similar to baseline scores.

Erythema, Scaling, Dryness, and Stinging/Burning were graded at Baseline and each post-Baseline visit on a scale of "0" (=None) to "3" (=Severe) scale. The results were similar for each of the signs and symptoms. The worst severity scores were generally mild or moderate, and rarely severe.

A summary of the worst severity scores in the subjects with Local Tolerability Assessments worse than baseline is provided in Table 10. Incidences for severe Local Tolerability scores ranged from 0.4% to 3.3% overall signs and symptoms.

TABLE 10

Summary of Local Tolerability Assessment - Percentages of Subjects with Scores Worse than Baseline (Safety Population):

| Timepoint | N | Erythema | N | Scaling | N | Dryness | N | Stinging/Burning |
|---|---|---|---|---|---|---|---|---|
| Week 1 (observed) | 423 | 29.3% | 423 | 40.2% | 423 | 45.2% | 423 | 50.8% |
| Week 2 (observed) | 429 | 19.8% | 429 | 29.4% | 429 | 31.5% | 429 | 24.0% |
| Month 1 (observed) | 415 | 16.1% | 415 | 20.5% | 415 | 25.5% | 415 | 19.3% |
| Month 2 (observed) | 426 | 13.4% | 426 | 16.4% | 426 | 21.6% | 426 | 11.5% |
| Month 4 (observed) | 389 | 4.6% | 389 | 8.0% | 389 | 11.8% | 389 | 5.9% |
| Month 6 (observed) | 361 | 7.8% | 361 | 7.8% | 361 | 9.1% | 361 | 6.4% |
| Month 8 (observed) | 341 | 7.9% | 341 | 10.0% | 341 | 13.8% | 341 | 8.2% |
| Month 10 (observed) | 329 | 7.0% | 329 | 9.1% | 329 | 11.9% | 329 | 7.3% |
| Month 12 (observed) | 327 | 5.5% | 327 | 4.6% | 327 | 9.2% | 327 | 5.8% |
| Final | 448 | 7.4% | 448 | 9.4% | 448 | 14.1% | 448 | 8.5% |
| Worst | 448 | 48.0% | 448 | 61.8% | 448 | 65.2% | 448 | 66.1% |

Final: The last available data observed during the post-Baseline period.
Worst: The data observed with the highest severity during the post-Baseline period.

Figure 2:
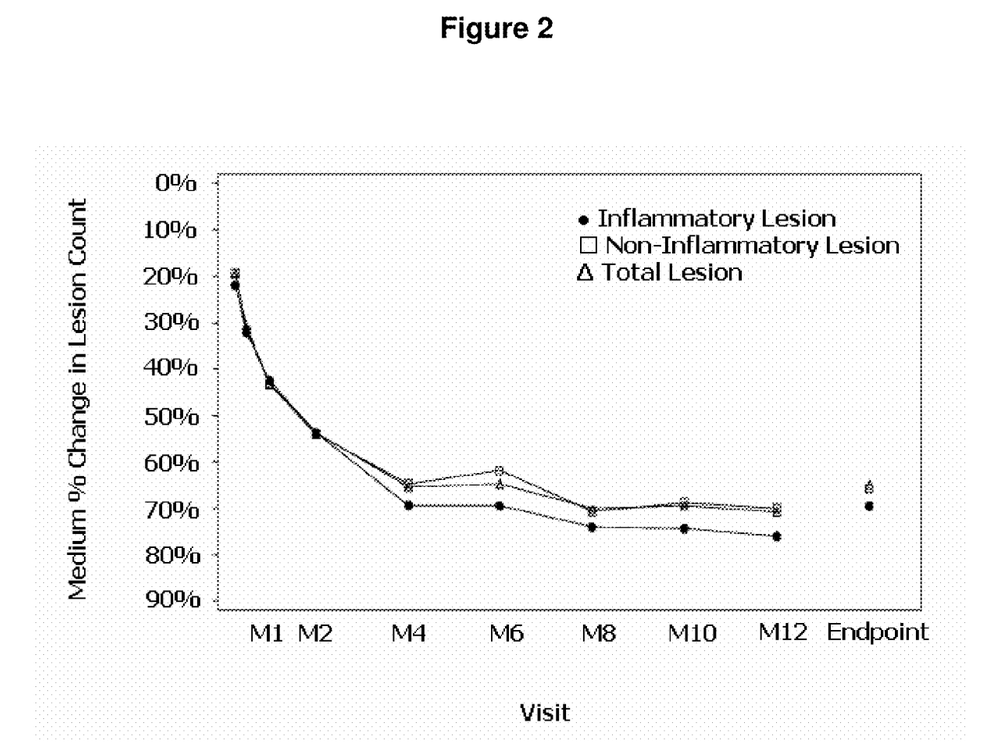
FIG. 2 shows time course of local cutaneous irritation (worse than baseline, observed data, and final score). Percentages of subjects with scores worse than baseline at each time point with endpoint.
Figure 3:
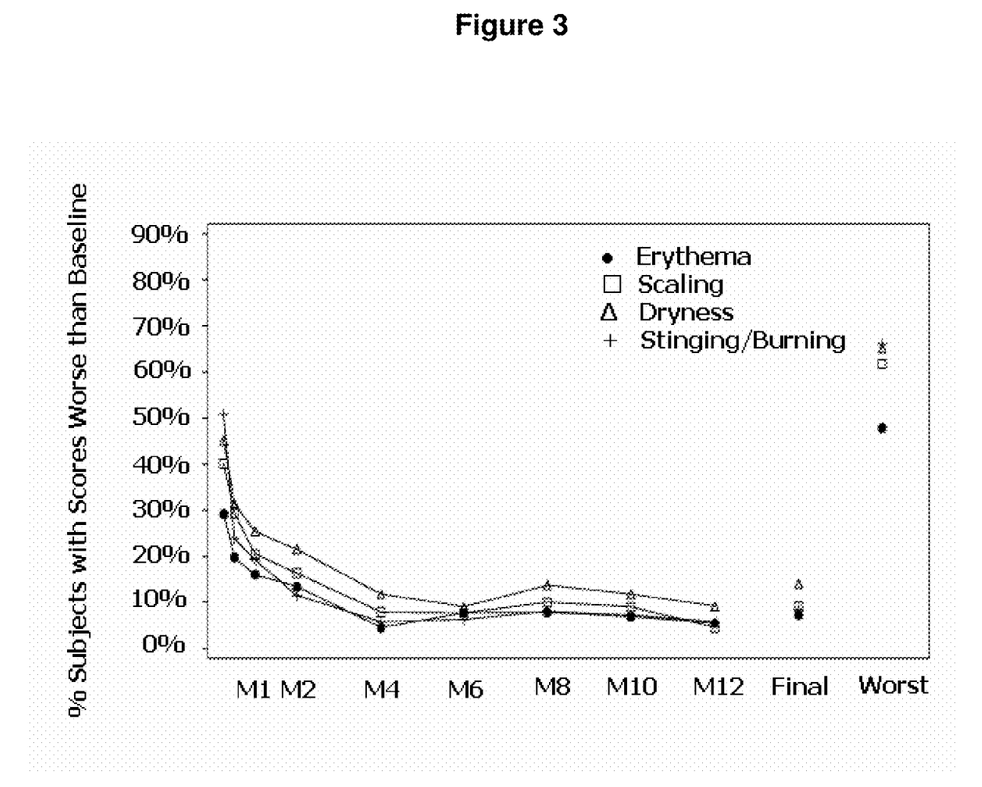
FIG. 3 shows the local Tolerability with representation of the Final Score and Worst Score (Safety Population).

Overall, treatment with adapalene-BPO was safe and well-tolerated when used for up to 12 months in subjects with acne vulgaris. The scores for the severity of erythema, scaling, dryness, and stinging/burning after study treatment are summarized in FIG. 2. Local cutaneous tolerability of the study treatment was good throughout the study, with mean tolerability scores for erythema, dryness, scaling, and burning/stinging all less than 1 (mild) at each study visit. The mean worst scores of all subjects were consistent with mild irritation. The highest mean cutaneous tolerability scores were The majority of Local Tolerability Assessment scores which were worse than the baseline scores were reported during the first week of treatment with Adapalene/Benzoyl Peroxide Gel for 29.3% of subjects for Erythema, 40.2% for Scaling, 45.2% for Dryness, and 50.8% for Stinging/Burning (Table 10). However, the incidence of Erythema, Scaling and Stinging/Burning decreased rapidly, and were reported by 10% or less subjects by Month 4. Incidences of Dryness were less than 12% by Month 4, and following Month 4 fluctuated from 9% to 14% for the remainder of the study.

Expected signs and symptoms of local cutaneous irritation were mild to moderate in severity. Very few subjects had severe scores. (Table 11).

TABLE 11

Summary of Local Tolerability Assessment
Worse than Baseline - Worst Scores (Safety Population):

| | Local Tolerability Worse than Baseline - Worst Score[a] (N = 448)[b] | | | |
|---|---|---|---|---|
| | | Worst Severity Score in these Subjects | | |
| Variable | Number of Subjects | Mild N (%) | Moderate N (%) | Severe N (%) |
| Erythema | 215 (48.0%) | 151 (33.7%) | 61 (13.6%) | 3 (0.7%) |
| Scaling | 277 (61.8%) | 225 (50.2%) | 50 (11.2%) | 2 (0.4%) |
| Dryness | 292 (65.2%) | 230 (51.3%) | 57 (12.7%) | 5 (1.1%) |
| Stinging/Burning | 296 (66.1%) | 185 (41.3%) | 96 (21.4%) | 15 (3.3%) |

[a]The data observed with the highest severity during the post-Baseline period for the subjects with data worse than Baseline.
[b]N = 448 is the number of subjects with local tolerability data available at Baseline and at least one post-baseline data point.

Adverse Events:

All AEs recorded on the case report forms (CRFs) are displayed in data listings.

AEs were also summarized for all subjects. A subject was counted only once per body system, even if more than one event was reported, and only once per COSTART (Coding Symbols for Thesaurus of Adverse Reaction Terms), even if more than one occurrence was reported.

The AE incidence by quarter was summarized for "Baseline to <3 months", "3 months to <6 months", "6 months to <9 months", and "9 months to 1 year." The AE incidence for each period was calculated as the number of subjects with AE onset dates within the period divided by the number of subjects at risk per period.

AE summary tables are listed in the Statistical Analysis Plan (SAP).

A summary of adverse events over the course of the study is shown in Table 12. Overall, 288 subjects (63.7%) experienced adverse events during the study. A total of 147 subjects (32.5%) had treatment-related adverse events (i.e., adverse event relationship to study drug assessed as "possible", "probable" or "definitely related"). The most common treatment-related adverse event was dry skin (17.3%) (table 13). The majority of adverse events were mild or moderate in severity. Most adverse events occurred within the first 3 months of therapy and the incidence dropped at subsequent visits. Only 19 subjects (4.2%) had severe adverse events and, of these, 10 subjects (2.2%) had severe adverse events deemed at least possibly related to study treatment. During the 12-month course of the study, only 9 subjects had 10 adverse events leading to discontinuation. Out of these 10 adverse events, 7 were related to study treatment.

TABLE 12

Overall Summary of Adverse Events (Safety Population):

| Category | Baseline to <Month 3 (N+ = 452) | Month 3 to <Month 6 (N+ = 397) | Month 6 to <Month 9 (N+ = 366) | Month 9 to Year (N+ = 334) | Total (N = 452) |
|---|---|---|---|---|---|
| Subjects With At Least One AE | 195 (43.1%) | 79 (19.9%) | 83 (22.7%) | 82 (24.6%) | 288 (63.7%) |
| Dermatological AE | 104 (23.0%) | 13 (3.3%) | 12 (3.3%) | 11 (3.3%) | 131 (29.0%) |
| Non-Dermatological AE | 139 (30.8%) | 72 (18.1%) | 77 (21.0%) | 78 (23.4%) | 243 (53.8%) |
| Subjects With At Least One AE Related To Study Drug | 127 (28.1%) | 16 (4.0%) | 11 (3.0%) | 5 (1.5%) | 147 (32.5%) |
| Dermatological AE | 94 (20.8%) | 8 (2.0%) | 8 (2.2%) | 4 (1.2%) | 110 (24.3%) |
| Non-Dermatological AE | 66 (14.6%) | 8 (2.0%) | 4 (1.1%) | 2 (0.6%) | 78 (17.3%) |
| Subjects With At Least One SAE | 1 (0.2%) | 2 (0.5%) | 1 (0.3%) | 1 (0.3%) | 5 (1.1%) |
| Dermatological AE | 0 | 0 | 0 | 0 | 0 |
| Non-Dermatological AE | 1 (0.2%) | 2 (0.5%) | 1 (0.3%) | 1 (0.3%) | 5 (1.1%) |
| Subjects With At Least One AE Leading to Disc. | 7 (1.5%) | 1 (0.3%) | 0 | 1 (0.3%) | 9 (2.0%) |
| Dermatological AE | 6 (1.3%) | 1 (0.3%) | 0 | 0 | 7 (1.5%) |
| Non-Dermatological AE | 1 (0.2%) | 0 | 0 | 1 (0.3%) | 2 (0.4%) |

Subjects may be counted twice, once in Dermatological category and once in Non-dermatological category for having more than one AE.

Related to study drug means that AE relationship to study drug was assessed as 'possible', 'probable' or 'definitely related'.

Subjects may be counted in more than one period due to multiple AEs. AE(s) with incomplete onset date(s) or onset date(s) prior to the first application are only included in the Total column.

N+=N at risk, the number of subjects at the beginning of each period.

TABLE 13

Most Frequent Adverse Events, Reported by at Least 1% of Total Subjects by System Organ Class and Preferred Term (Safety Population):

| System Organ Class/Preferred Term* | Baseline to <Month 3 (N+ = 452) | Month 3 to <Month 6 (N+ = 397) | Month 6 to <Month 9 (N+ = 366) | Month 9 to 1 Year (N+ = 334) | Total (N = 452) |
|---|---|---|---|---|---|
| Total Number of AE(s) | 405 | 113 | 125 | 108 | 766 |
| Total Number (%) of Subjects with AE(s) | 195 (43.1%) | 79 (19.9%) | 83 (22.7%) | 82 (24.6%) | 288 (63.7%) |
| Infections and Infestations | 48 (10.6%) | 33 (8.3%) | 39 (10.7%) | 49 (14.7%) | 135 (29.9%) |
| Nasopharyngitis | 14 (3.1%) | 7 (1.8%) | 9 (2.5%) | 8 (2.4%) | 30 (6.6%) |
| Upper Respiratory Tract Infection | 7 (1.5%) | 0 | 11 (3.0%) | 9 (2.7%) | 26 (5.8%) |
| Influenza | 4 (0.9%) | 2 (0.5%) | 2 (0.5%) | 10 (3.0%) | 18 (4.0%) |
| Sinusitis | 6 (1.3%) | 3 (0.8%) | 3 (0.8%) | 5 (1.5%) | 15 (3.3%) |
| Pharyngitis Streptococcal | 5 (1.1%) | 2 (0.5%) | 3 (0.8%) | 3 (0.9%) | 13 (2.9%) |
| Urinary Tract Infection | 1 (0.2%) | 3 (0.8%) | 0 | 4 (1.2%) | 8 (1.8%) |
| Gastroenteritis Viral | 2 (0.4%) | 1 (0.3%) | 2 (0.5%) | 3 (0.9%) | 7 (1.5%) |
| Bronchitis | 0 | 3 (0.8%) | 1 (0.3%) | 3 (0.9%) | 7 (1.5%) |
| Skin and Subcutaneous Tissue Disorders | 104 (23.0%) | 13 (3.3%) | 12 (3.3%) | 11 (3.3%) | 131 (29.0%) |
| Dry Skin | 71 (15.7%) | 5 (1.3%) | 6 (1.6%) | 3 (0.9%) | 80 (17.7%) |
| Erythema | 22 (4.9%) | 1 (0.3%) | 2 (0.5%) | 1 (0.3%) | 25 (5.5%) |
| Skin Desquamation | 22 (4.9%) | 0 | 1 (0.3%) | 0 | 23 (5.1%) |
| Contact Dermatitis | 12 (2.7%) | 1 (0.3%) | 2 (0.5%) | 2 (0.6%) | 17 (3.8%) |
| Pruritus | 4 (0.9%) | 0 | 2 (0.5%) | 1 (0.3%) | 7 (1.5%) |
| Acne | 3 (0.7%) | 2 (0.5%) | 0 | 0 | 5 (1.1%) |
| Swelling Face | 4 (0.9%) | 0 | 1 (0.3%) | 1 (0.3%) | 5 (1.1%) |
| Skin Discomfort | 5 (1.1%) | 0 | 0 | 0 | 5 (1.1%) |
| General Disorders and Administration Site Conditions | 63 (13.9%) | 5 (1.3%) | 7 (1.9%) | 2 (0.6%) | 74 (16.4%) |
| Application Site Burning | 57 (12.6%) | 3 (0.8%) | 4 (1.1%) | 1 (0.3%) | 64 (14.2%) |
| Application Site Irritation | 16 (3.5%) | 1 (0.3%) | 0 | 1 (0.3%) | 18 (4.0%) |
| Injury, Poisoning and Procedural Complications | 21 (4.6%) | 18 (4.5%) | 5 (1.4%) | 4 (1.2%) | 47 (10.4%) |
| Sunburn | 11 (2.4%) | 8 (2.0%) | 1 (0.3%) | 2 (0.6%) | 21 (4.6%) |
| Joint Sprain | 2 (0.4%) | 1 (0.3%) | 0 | 1 (0.3%) | 5 (1.1%) |
| Respiratory, Thoracic and Mediastinal Disorders | 9 (2.0%) | 6 (1.5%) | 13 (3.6%) | 3 (0.9%) | 29 (6.4%) |
| Pharolaryngeal Pain | 4 (0.9%) | 4 (1.0%) | 5 (1.4%) | 1 (0.3%) | 14 (3.1%) |
| Nasal Congestion | 1 (0.2%) | 1 (0.3%) | 2 (0.5%) | 1 (0.3%) | 5 (1.1%) |
| Gastrointestinal Disorders | 14 (3.1%) | 8 (2.0%) | 6 (1.6%) | 4 (1.2%) | 28 (6.2%) |
| Vomiting | 4 (0.9%) | 1 (0.3%) | 2 (0.5%) | 0 | 6 (1.3%) |

TABLE 13-continued

Most Frequent Adverse Events, Reported by at
Least 1% of Total Subjects by System Organ Class and Preferred Term
(Safety Population):

| System Organ Class/Preferred Term* | Baseline to <Month 3 (N+ = 452) | Month 3 to <Month 6 (N+ = 397) | Month 6 to <Month 9 (N+ = 366) | Month 9 to 1 Year (N+ = 334) | Total (N = 452) |
|---|---|---|---|---|---|
| Nausea | 1 (0.2%) | 1 (0.3%) | 3 (0.8%) | 1 (0.3%) | 6 (1.3%) |
| Nervous System Disorders | 16 (3.5%) | 5 (1.3%) | 1 (0.3%) | 5 (1.5%) | 25 (5.5%) |
| Headache | 16 (3.5%) | 4 (1.0%) | 1 (0.3%) | 3 (0.9%) | 21 (4.6%) |

*Multiple occurrences within a System Organ Class (SOC) by a subject were counted once per SOC. Multiple occurrences of a Preferred Term by a subject were counted once per Preferred Term. A subject was counted once even if the subject experienced more than one AE during the study. Subjects may be counted in more than one period due to multiple AEs. AE(s) with incomplete onset date(s) or onset date(s) prior to the first application are only included in the Total column.
N+ = N at risk, the number of subjects at the beginning of each period.

Five subjects (5/452, 1.1%) had a total of 6 serious adverse events (depression, staphylococcal infection, clavicle fracture, syncope, bipolar disorder and drug abuse), all of which were non-dermatologic and unrelated to the study drug. There were no deaths during the study and no confirmed cases of sensitization occurred in the study. Over the course of the one year, no clinically relevant drug-related changes in routine laboratory parameters (clinical chemistry, hematology and urinalysis) were observed. Ten subjects (10/452, 2.2%) had clinically significant post-baseline laboratory assessments reported as adverse events, although these were not considered treatment-related.

This study is the first long-term clinical evaluation of the safety and efficacy of a unique fixed-dose combination of a retinoid (adapalene 0.1%) and BPO 2.5%. This once-daily combination addresses multiple pathogenic factors of acne, providing prompt and sustained efficacy with no risk for antibiotic resistance. Overall, the results of the study support the safe and effective use of the fixed-dose combination gel of adapalene and BPO for the long-term management of subjects with acne vulgaris. In terms of safety, most adverse events and symptoms of skin irritation were mild-to-moderate, occurred early in the study, and were transient. The use of a daily moisturizer when starting therapy may help to avoid the most common adverse events, like dry skin. Importantly, there was a low rate of discontinuation due to adverse events (2.0%) and no subjects discontinued due to lack of efficacy. Clinically significant inflammatory and non-inflammatory lesion count reductions were observed as early as week 1 and were sustained for up to 1 year. Eighty percent (80%) of subjects reported moderate, marked, or complete improvement of their acne. Results of this study are consistent with a previous 12-week, double-blind controlled study, which showed the adapalene-BPO combination produced significantly greater lesion reductions and had a quicker onset of action relative to corresponding monotherapies, with a comparable safety profile to adapalene.

Since acne is a chronic disease, its management often requires a long-term therapeutic strategy to control acne and maintain improvements. For all but the most severe acne, combination therapy with agents with complementary mechanisms of action should be utilized as early as possible and then followed with a maintenance therapy. As observed in this study, the use of the adapalene-BPO fixed-dose combination can be use for both initiation and long-term therapy for moderate to severe acne.

Previous studies have shown that the use of combination therapy with adapalene gel 0.1% may be more tolerable and associated with a lower rate of adverse events relative to the other topical retinoids.[25-29] Consistent with these prior experiences, adapalene when combined with BPO in a fixed-dose formulation was well tolerated in pre-clinical studies, a large double-blind controlled clinical study, and in the current long-term study, with a similar safety and tolerability profile as adapalene monotherapy. Furthermore, a well-tolerated fixed-dose combination therapy may also be more convenient and simplify a acne treatment regimen, thereby potentially improving treatment adherence.

The results of this study are compatible with those reported in recently published acne maintenance studies. Acne lesions have been shown to return after discontinuing a combination treatment regimen and therefore long-term therapy is necessary for many acne patients. In this study, acne lesions continued to decrease from baseline to approximately month 4 and the therapeutic effect was sustained throughout the year. There are several published studies demonstrating the value of long-term treatment following successful initial therapy to help limit the development of subclinical microcomedones and thereby prevent the recurrence of the disease after initial improvement. For example, Thiboutot et al assessed the maintenance effect of adapalene 0.1% gel relative to gel vehicle in 253 subjects successfully treated in a previous adapalene-doxycycline combination therapy study. This 16-week study demonstrated a significant clinical benefit of continued treatment with adapalene 0.1% gel relative to vehicle. Although future studies will be needed to properly evaluate adapalene-BPO as a maintenance therapy, the long-term safety and efficacy results of the current study suggest that expanding the armamentarium available for acne management with this fixed-dose combination will provide greater flexibility for customizing both short- and long-term care.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed:

1. A regimen for the safe and effective long-term treatment of acne vulgaris, comprising topically applying onto an affected skin area of a subject afflicted therewith, at least once every two days for a period of time of at least six (6) months, a thus effective amount of a topical medicament which comprises a fixed-dose combination of 0.1% to 0.3% by weight of adapalene and 2.5% by weight of benzoyl peroxide, formulated into a pharmaceutically acceptable medium therefor, said adapalene and said benzoyl peroxide being the only anti-acne active ingredients in said fixed-dose combination, the percentage by weight being relative to the total weight of the topical medicament.

2. The regimen for long-term treatment of acne vulgaris as defined by claim 1, comprising administering said topical medicament for at least twelve (12) months.

3. The regimen for the long-term treatment of acne vulgaris as defined by claim 1, comprising administering said topical medicament for at least nine (9) months.

4. The regimen for long-term treatment of acne vulgaris as defined by claim 1, comprising administering said topical medicament once a day.

5. The regimen for long-term treatment of acne vulgaris as defined by claim 1, comprising administering said topical medicament every two (2) days.

6. The regimen for the long-term treatment of acne vulgaris as defined by claim 1, comprising administering said topical medicament in the evening after washing said affected skin area.

7. The regimen for the long-term treatment of acne vulgaris as defined by claim 1, said topical medicament comprising a gel composition.

8. The regimen for the long-term treatment of acne vulgaris as defined by claim 4, comprising administering said topical medicament for at least nine (9) months.

9. The regimen for the long-term treatment of acne vulgaris as defined by claim 4, comprising administering said topical medicament for at least twelve (12) months.

10. The regimen for the long-term treatment of acne vulgaris as defined by claim 1, wherein the topical medicament comprises 0.1% by weight of adapalene and 2.5% by weight of benzoyl peroxide, relative to the total weight thereof.

11. The regimen for the long-term treatment of acne vulgaris as defined by claim 1, said affected skin area containing from 20 to 100 non-inflammatory lesions, 20 to 50 inflammatory lesions, and no active nodules or cysts.

* * * * *